United States Patent [19]
Smith et al.

[11] Patent Number: 5,588,428
[45] Date of Patent: Dec. 31, 1996

[54] METHOD AND APPARATUS FOR NON-INVASIVE VOLUME AND TEXTURE ANALYSIS

[75] Inventors: Daniel J. Smith, Stow; Shailesh Bhat, Akron, both of Ohio

[73] Assignee: The University of Akron, Akron, Ohio

[21] Appl. No.: 54,797

[22] Filed: Apr. 28, 1993

[51] Int. Cl.$^6$ .......................... G06F 159/00; A61B 5/05; A61B 6/00
[52] U.S. Cl. ................................. 128/653.1; 128/660.01; 128/665; 382/128; 73/601
[58] Field of Search ........................ 364/413.13, 413.15, 364/413.19, 413.22, 413.25, 474.05, 474.08, 506, 550, 561, 562, 563, 564; 250/458.1, 459.1, 461.1, 461.2, 305, 306, 442.11; 356/2, 18, 32, 33, 445, 39, 237, 256; 367/907; 73/601, 597, 598, 606; 382/108, 128; 128/660.07, 653.1, 660.01, 915, 916, 662.06, 665

[56] References Cited

U.S. PATENT DOCUMENTS

| | | | |
|---|---|---|---|
| 3,790,281 | 2/1974 | Kessler et al. | 356/72 |
| 3,792,422 | 2/1974 | Ernvein-Pecquenard | 367/10 |
| 3,910,701 | 10/1975 | Henderson et al. | 356/39 |
| 4,289,140 | 9/1981 | Carpenter et al. | 128/660.07 |
| 4,457,311 | 7/1984 | Sorenson et al. | 128/661.01 |

(List continued on next page.)

FOREIGN PATENT DOCUMENTS

| | | |
|---|---|---|
| 9009757813 | 6/1989 | European Pat. Off. . |
| 9012535 | 11/1990 | Japan . |

OTHER PUBLICATIONS

Three-dimensional Input of Body Surface Data Using a Laser Scanner; C. Cutting et al; Annal of Plastic Surgery vol. 21, No. 1, Jul., 1988.

(List continued on next page.)

Primary Examiner—Robert A. Weinhardt
Assistant Examiner—Joseph Thomas
Attorney, Agent, or Firm—Renner, Kenner, Greive, Bobak, Taylor & Weber

[57] ABSTRACT

The invention is directed to non-invasive methods and apparatus for three-dimensional measurement of surface profile and/or volume, and analysis of surface texture for evaluation of wound repair, assessment of surgical reconstructions or treatment of hypertrophic scarring, evaluation of polymerization reactions for polymer and elastomeric curing processes, or in any industrial process requiring quantitative monitoring of surface texture and profile. Both volume and surface texture are quantitatively measured very accurately, and the apparatus and method can be used on both soft and hard surfaces according to the above objectives. The invention generally comprises an apparatus and method to image a three-dimensional surface for volumetric analysis and/or surface texture. The apparatus includes a laser source for emitting a predetermined wavelength beam which is reflected off the surface being imaged, and a laser detector or sensor positioned relative to the laser source for receiving the reflected beam to generate a first signal corresponding to the amount of laser energy reflected off the surface. The reflected beam is indicative of changes in the depth of the surface relative to the laser source, and can therefore be used to monitor changes in surface depth. Further, a sound source is provided for generating a coherent beam of sound waves which are reflected off the surface also. A sound detector positioned relative to the sound source receives reflected sound waves to generate at least a second signal corresponding to the amount of sound waves reflected off the surface, wherein the reflected sound waves are a measure of the surface texture. A control system selectively operates the laser source and sound source for generating the signals at a plurality of locations on the surface for analysis. The apparatus may be portable, and provides a quick and accurate quantitative measurement of a surface, and can be used in association with both hard and soft surfaces.

19 Claims, 6 Drawing Sheets

U.S. PATENT DOCUMENTS

| | | | |
|---|---|---|---|
| 4,627,734 | 12/1986 | Rioux | 356/376 |
| 4,672,969 | 6/1987 | Dew | 128/397 |
| 4,680,084 | 7/1987 | Heimman et al. | 156/626 |
| 4,686,986 | 8/1987 | Fenyö et al. | 607/90 |
| 4,703,758 | 11/1987 | Omura | 128/672 |
| 4,721,379 | 1/1988 | L'Esperance | 351/212 |
| 4,747,411 | 5/1988 | Ledley | 128/660.07 |
| 4,763,282 | 8/1988 | Rosenberg | 364/524 |
| 4,768,513 | 9/1988 | Suzuki | 128/634 |
| 4,833,469 | 5/1989 | David | 340/901 |
| 4,836,212 | 6/1989 | Schmitt et al. | 128/667 |
| 4,842,411 | 6/1989 | Wood | 356/376 |
| 4,894,547 | 1/1990 | Leffell et al. | 250/461.2 |
| 4,896,343 | 1/1990 | Saunders | 378/95 |
| 4,947,351 | 8/1990 | Moran et al. | 364/507 |
| 4,965,840 | 10/1990 | Subbarao | 382/1 |
| 4,970,054 | 11/1990 | Mori | 422/108 |
| 4,973,154 | 11/1990 | McMichael et al. | 356/4.5 |
| 4,979,815 | 12/1990 | Tsikos | 356/1 |
| 4,986,664 | 1/1991 | Lovoi | 356/376 |
| 4,989,984 | 2/1991 | Salinger | 356/445 |
| 5,005,975 | 4/1991 | Kawai et al. | 356/237 |
| 5,016,173 | 5/1991 | Kenet et al. | 364/413.13 |
| 5,055,679 | 10/1991 | Ninomiya et al. | 250/306 |
| 5,074,306 | 12/1991 | Green et al. | 128/664 |
| 5,088,493 | 2/1992 | Giannini et al. | 128/633 |
| 5,140,984 | 8/1992 | Dew et al. | 128/395 |
| 5,154,680 | 10/1992 | Drzewiecki et al. | 128/672 |
| 5,224,175 | 6/1993 | Gouge et al. | 382/6 |
| 5,224,481 | 7/1993 | Ishihara et al. | 128/660.07 |
| 5,241,468 | 8/1993 | Kenet | 364/413.01 |
| 5,259,380 | 11/1993 | Mendes et al. | 607/115 |
| 5,278,776 | 1/1994 | Fisher et al. | 364/508 |
| 5,291,890 | 3/1994 | Cline et al. | 128/653.2 |
| 5,344,433 | 9/1994 | Talmore | 607/88 |

OTHER PUBLICATIONS

Measurement of Pressure Ulcer Volume Using Dental Impression Materials: Suggestion from the Field; J. Covington et al; Physical Therapy vol. 69, No. 8, Aug., 1989.

Stereophotography and Computerized Image Analysis: A Three–Dimensional Method of Measuring Wound Healing; R. Frantz et al; Wounds: A Compendium of Clinical Research and Practice vol. 4, No. 2. Mar./Apr. 1992.

Quantitative acoustical assessment of wound maturation with acoustic microscopy; W. D. O'Brien et al; J. Acoust. Soc. Am. 69(2), Feb. 1981.

"Selective Laser Sintering . . . ", Bartels, et al., Biomedical Sciences Instrumentation, pp. 243–250 of vol. 29, presented Apr. 23, 1993.

"A Software System for Interactive and Quantitative Visualization . . . " Robb, et al., Australasian Physical & Engineering Sciences in Medicine, (1991) vol. 14, No. 1, pp. 9–30.

Dialog File 5, Acc. No. 5893175: Olerud, et al: "Ultrasonic Assessment of Skin & Wounds . . . ", Journal of Investigative Derma., 88(5) 1987, pp. 615–623.

FIG.-12

METHOD AND APPARATUS FOR NON-INVASIVE VOLUME AND TEXTURE ANALYSIS

TECHNICAL FIELD

This invention is generally directed to methods and apparatus for performing non-invasive three dimensional measurement of surface profile and/or volume, and analysis of surface texture of various hard and soft surfaces, for medical and industrial applications. More particularly, the invention is directed to a method and apparatus for quantitative measurement of volume and surface texture analysis utilizing a combination of a non-contact laser and sound scanner, particularly useful for analysis and monitoring of skin wounds or other skin surfaces non-invasively.

BACKGROUND OF THE INVENTION

In the area of wound repair and clinical wound management, a quantitative method for assessing wound healing is necessary or at least extremely desirable. The cost of treating wounds, particularly chronic, non-healing wounds is quite large, in terms of health care costs as well as pain and suffering of the patient under these circumstances. As the number of individuals suffering from non-healing wounds will most likely increase due to the increasing general age of the population as well as increase in life expectancy, there has been found a need to assess wound healing in vivo, for which various methods and techniques have been utilized. In vivo assessment of wound repair has developed using various methodologies, including both subjective and objective methods, and superficial methods or more detailed wound assessment which attempts to quantitatively analyze wound healing.

Superficial wound assessment may be performed by subjective or objective tests, including analysis of pain, erythema, induration, and edema, these subjective assessments being of no particular help in quantitatively measuring and evaluating wound healing. Objective methods which do allow some quantitative assessment of wound repair include direct measurement of wound size, wound mapping, wound photography, and volumetric measurement of wounds. For more detailed wound assessment and quantitative measurements, various approaches have been adopted, which include invasive and non-invasive techniques. Invasive assessment of wound healing may be performed by biochemical analysis of wound fluids and/or tissue and can give valuable information particularly with regard to the inflammatory stage of wound healing. Histological evaluation of wound tissue has also provided information on the structure and components of the wound, and has supported a significant role for macrophages in the control and stimulation of wound repair. Another invasive technique includes monitoring of granulation tissue formation on the wound, indicating the influx of macrophages, fibroblasts, and neovasculature into the wound. Invasive techniques to monitor granulation tissue formation have been developed for various aspects of this formation. Additionally, blood perfusion in a wound may be correlated to the angiogenic response of the wound, and techniques such as angiography after an injection of a suitable dye, electron-microscopy and histological or immunohistochemical techniques have been developed in this regard. Finally, matrix formation and the accumulation of collagen in the wound is a final portion of the wound reparative process, and measurement of tensile strength of the wound or biochemical methods of analysis of the wound may be used.

As should be recognized, such invasive techniques are not extremely desirable for human patients, and do not allow repeated, reproducible measurements of a single wound while not interfering with the healing process. These methods do not allow time course studies of a wound to assess treatment procedures or the like. Thus, non-invasive methods to evaluate wound healing have been developed so as not to induce trauma to the wound during the healing process, and allow time course studies of a wound. Several techniques for non-invasively assessing wound healing include laser doppler flowmetry, which can be utilized to measure perfusion and angiogenesis in the healing of a wound, ultrasonic pulse echo techniques yielding a two-dimensional image of the wound, transcutaneous gas monitoring to measure the levels of oxygen and carbon dioxide released from the healing tissue, stereophotogrammetry for measurement of wound volumes, video image analysis, and tensometry which non-invasively measures the tensile strength of a wound. Although each of these non-invasive methods is beneficial in that no induced trauma to the wound will occur, none gives accurate and repeatable measurements of a wound throughout the healing cycle which will allow quantitative assessment of treatment procedures used in the healing process. For example, growth factors are increasingly used in wound treatment, as well as other new treatments typically based on final wound closure. No existing quantitative methods provide reliable early indicators of wound healing without significant effort or expense resulting in lengthy clinical trials and extensive patient care with increased cost. Further, as the number of effective treatments grows, it becomes more difficult to determine the optimal therapy for a particular wound situation, particularly if no quantitative analysis or assessment tool is available. There has therefore been found a need to provide a simple, non-invasive system to detect subtle but important changes in healing tissue, particularly during early stages of wound repair.

As an alternative to the assessment of wound healing, there has also been found to be a need to accurately measure surface profiles and textures in a variety of applications. For example, such measurements are desirable in plastic surgery or other surgical reconstructions or treatment of hypertrophic scarring, and yet no means for quantitative analysis is generally available. Apart from medical use, any industrial process which requires monitoring of surface texture and profile may benefit from a quantitative measurement tool which is accurate and cost effective in its operation. Non-invasive three-dimensional measurement of surface profile, volume and analysis of surface texture is therefore desirable in a variety of medical and industrial applications, and there therefore is a distinct need for a method and apparatus for such analysis.

SUMMARY OF THE INVENTION

Based upon the foregoing, the present invention is directed to non-invasive methods and apparatus for three-dimensional measurement of surface profile and/or volume, and analysis of surface texture for evaluation of wound repair, assessment of surgical reconstructions or treatment of hypertrophic scarring, evaluation of polymerization reactions for polymer and elastomeric curing processes, or in any industrial process requiring quantitative monitoring of surface texture and profile. Both volume and surface texture are quantitatively measured very accurately, and the apparatus and method can be used on both soft and hard surfaces according to the above objectives. The invention generally comprises an apparatus and method to image a three-dimensional surface for volumetric analysis and/or surface texture. The apparatus includes a laser source for emitting a predetermined wavelength beam which is reflected off the surface being imaged, and a laser detector or sensor positioned relative to the laser source for receiving the reflected beam to generate a first signal corresponding to the amount of laser energy reflected off the surface. The reflected beam is indicative of changes in the depth of the surface relative to the laser source, and can therefore be used to monitor changes in surface depth. Further, a sound source is provided for generating a coherent beam of sound waves which are reflected off the surface also. A sound detector positioned relative to the sound source receives reflected sound waves to generate a second signal corresponding to the amount of sound waves reflected off the surface, wherein the reflected sound waves are a measure of the surface texture. A third signal which may also be generated from the sound source and detector if desired, corresponds to monitoring the delay in time of the reflected sound waves, which is also indicative of changes in the depth of the surface relative to the sound source. Control means for selectively operating the laser source and sound source are provided for generating the first, second, and possibly the third signal at a plurality of locations on the surface for analysis. The apparatus includes processing means to receive and process the laser and sound signals to generate an image of the surface and acquire volumetric and textural measurements.

The apparatus may be portable, and provides a quick and accurate quantitative measurement of a surface, and can be used in association with both hard and soft surfaces.

The apparatus is particularly useful for non-invasively analyzing surface profiles and surface texture in a method which includes the steps of reflecting a laser beam off a portion of the surface and detecting the reflected beam to determine the position of the portion of the surface relative to the source of the laser beam. Simultaneously or in a separate operation, a coherent beam of sound waves is reflected off the same portion of the surface, and reflected sound waves are detected to determine at least the texture of the surface at this location. These steps are repeated a plurality of times to scan over the surface, and thereafter an image of the scanned surface can be generated to quantitatively measure profile and surface textural changes over the scanned surface. In a particular application, the apparatus and method may be utilized for evaluating wound repair, with such evaluation further including the steps of repeating the scanning operation at discrete time intervals and comparing the generated images of the wound to quantitatively analyze and visualize wound healing during re-epithelialization of the wound surface and the formation of granulation tissue associated with wound healing to allow evaluation of wound repair over a predetermined period of time.

BRIEF DESCRIPTION OF THE DRAWINGS

The objects and advantages of the apparatus and methods of the invention will become apparent upon a reading of the detailed description of the invention in conjunction with the drawings, wherein.

DETAILED DESCRIPTION OF THE INVENTION

Figure 1:
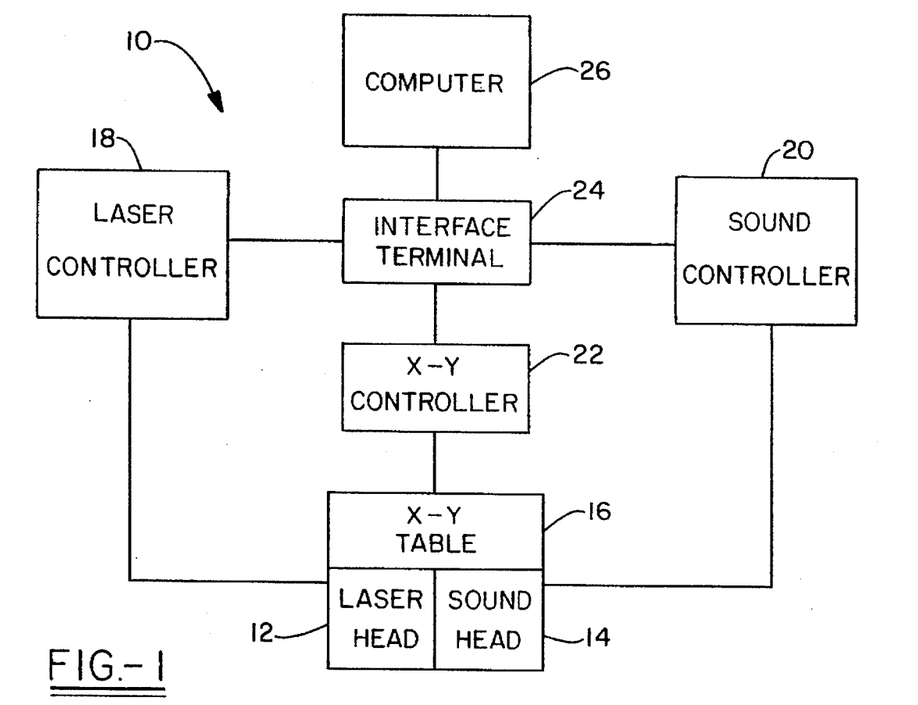
FIG. 1 is a schematic diagram of the imaging apparatus of the invention.

Turning to FIG. 1, the apparatus of the invention is shown in a generalized block diagram form indicating various components of a preferred embodiment. The apparatus generally designated 10 is utilized to non-invasively measure surface profile and/or volume of three-dimensional surface along with analysis of surface texture along the surface. The apparatus is used to generate an image of a surface, and may be used in various medical or industrial applications. The apparatus 10 includes a laser head 12, which itself includes both a source of laser energy as well as a sensor or detector associated therewith. Generally, light emitted from the laser source of laser head 12 is converged to substantially a point on the surface to be analyzed. The converged beam of light from laser head 12 will be scattered from the surface and detected to yield an indication of the distance from the laser source to the surface at the predetermined point on the surface. A plurality of such points are used in a scanning procedure to yield information regarding the surface profile along a scan line or lines, and from this a measure of the volume of a surface depression or the like can be calculated. The apparatus further includes a sound head 14, which has a source of sound for producing sound waves which are reflected off the surface being analyzed and subsequently detected by a sound sensor associated with sound head 14. The sound head 14 is utilized at least in a capacity to analyze the texture of surface under test, wherein the percent of sound waves reflected from the surface is indicative of the surface texture. Both the laser head 12 and sound head 14 may be mounted on a positioning means, which as indicated in FIG. 1 may comprise an inverted X-Y Table 16. The positioning table 16 will allow movement of the laser head 12 and sound head 14 relative to a surface under test, which in the preferred embodiment is desirable to avoid the need to move the surface under test for scanning thereof. The positioning table 16 allows two-dimensional movement of the laser head 12 and sound head 14 for scanning of any desired portion of a surface in a repeatable and accurate manner.

Associated with laser head 12, is a laser controller 18, which is utilized to control operation of laser head 12 to effect scanning of a surface in association with the positioning table 16. The laser controller 18 will control operation of the laser source and sensor associated with laser head 12, and will allow data to be gathered during a scanning procedure for a plurality of points on the surface being analyzed. The laser controller 18 will allow adjustment of the position range of the emitted laser light, the span range as well as the resolution of the laser beam being utilized. The laser controller 18 may also be used to control other functions of the laser head 12 as desired. Similarly, the sound head 14 is coupled to a sound controller 20, which enables operation of the sound head 14 to perform scanning of a surface in association with the positioning table 16. The sound controller 20 will allow adjustment of the measuring range of the sound head 14, the sampling rate of the sound sensor associated therewith, and may also include means for calibrating the sound head 14 and associated processing circuitry to perform various processing procedures on analog electrical signals produced by the sound sensor. The positioning table 16 of the apparatus also is coupled to a controller 22, which may be used to control movement of the positioning table 16 and the associated laser head 12 and sound head 14 mounted thereon. To perform scanning procedures, the positioning table 16 is moved in discrete increments to adjust the position of laser head 12 and sound head 14 relative to the surface under test. Each of the controllers 18, 20, and 22 are coupled to an interface terminal 24 which is interfaced with a computer or processing means 26. The computer 26 is therefore utilized to control operation of the laser head 12 by means of laser controller 18, and of sound head 14 by means of sound controller 20. The computer 26 is also utilized to control scanning functions implemented by the X-Y controller 22 and X-Y table 16 on which the sensors 12 and 14 are positioned. In addition to controlling operation of the various components in the apparatus, computer 26 will also be used in acquisition of data from both the laser head 12 and sound head 14, and will process the acquired data to generate an image of the surface under test for analysis.

In a preferred embodiment of the invention, the laser head 12 may be of the type produced by Keyence Corporation of Fairlawn, N.J., Model #LB-12, which is semi-conductor laser emitting a 3 mW beam of light having a diameter of 1 mm at a wavelength of 780 nm. Pulses of light are produced by the laser source, with pulses having a duration of up to 15 microseconds achievable. The resolution of this laser head may be as small as 2 μm, with the beam spot being focused at approximately a distance of 100 mm from the laser emitting portion of the laser head 12. Although this specific laser head has been used to obtain good results in the apparatus, it is understood and contemplated within the invention that a variety of laser sources may be utilized to obtain higher accuracy, adjustment of working distance, compatibility with a human patient or the like. As the apparatus may be used in association with non-invasive analysis of wounds, the laser head 12 in such an embodiment will be of a type which will not affect the wound surface nor cause any discomfort to a patient. Along with the specific laser head as identified above, a specific laser controller 18 usable with the invention is also produced by the Keyence Corp., Model #LB-72. Such a laser controller in association with the laser previously mentioned will allow adjustment of the position range between 30 to 50 mm from the wound surface, as well as allowing adjustment of the span range of an analog output voltage produced by the laser sensor in head 12. The span range may be adjusted between 0.4 V/mm plus or minus 30%, and additional adjustment may be provided by span adjustor trimmers within the controller. Resolution of the laser beam may also be controlled by means of this controller between 2–50 μm as desired for a particular application.

A specific example of a sound head 14 usable in the apparatus may be a sonic sensor produced by Cleveland Machine Controls, Inc. of Cleveland, Ohio, and particularly their Pulsonic 5000 Series Parabolic Head Sensor. This sonic sensor produces a coherent column of 140 kHz sound waves which are focused to substantially a point on a surface to be analyzed. For example, the sound waves from this sensor may be focused to substantially a point having a diameter of 0.125". In association with such a sensor, a sonic sensor controller also produced by Cleveland Machine Controls, Inc. will allow adjustment of the measuring range (12.7±10 mm) and the sampling rate (maximum of 800 Hz). Such a controller also provides a precise 0–10 VDC calibration signal output which is directly proportional to the distance measured and the sound wave amplitude variation. This controller also contains an analog conditioner module which allows signal offset, gain, and signal inversion adjustments.

The interface terminal 24 of the apparatus may be provided as a circuit which will be coupled to the laser controller 18, sound controller 20, and X-Y controller 22, for controlling each of the measurement heads and scanning procedures, as well as for processing analog signals generated by the laser head 12 and sound head 14 and coupling these signals to computer 26. The interface 24 may therefore include analog processing circuitry to receive analog signals generated by laser head 12 and sound head 14 for normalization or amplification of these signals. The interface 24 will thereafter couple the analog signals to computer 26, which in a preferred embodiment comprises a personal computer having an analog to digital converter board installed therein. Output signals from the laser and sound sensors are converted to digital signals, and acquisition of these signals as well as analysis and processing of the signals is performed using suitable software associated with the PC. Also in the apparatus, the X-Y Table 16 may be a positioning table produced by Velmex, Inc. of Bloomfield, N.J., which is inverted and mounted to an aluminum frame. Lead screws associated with the table to effect movement in two dimensions are connected to two-phase stepper motors, which in a particular example will produce 1.8° of movement per step. Associated with the stepper motors may be stepper motor controllers also produced by Velmex, Inc., Model #NF90, which move the X-Y Table with a minimum $6.25 \times 10^{-5}$ inches per step at a resolution of 400 steps per revolution. The stepper motor controller can be programmed to index from 1–6000 steps per second in increments of 1 step per second. It again should be recognized that each of the specific components mentioned above are merely examples of suitable components which can be utilized in the apparatus of the invention. It is contemplated within the scope of the invention that alternative equipment may be used for each of the separate components to achieve the desired attributes of the apparatus.

Figure 2:
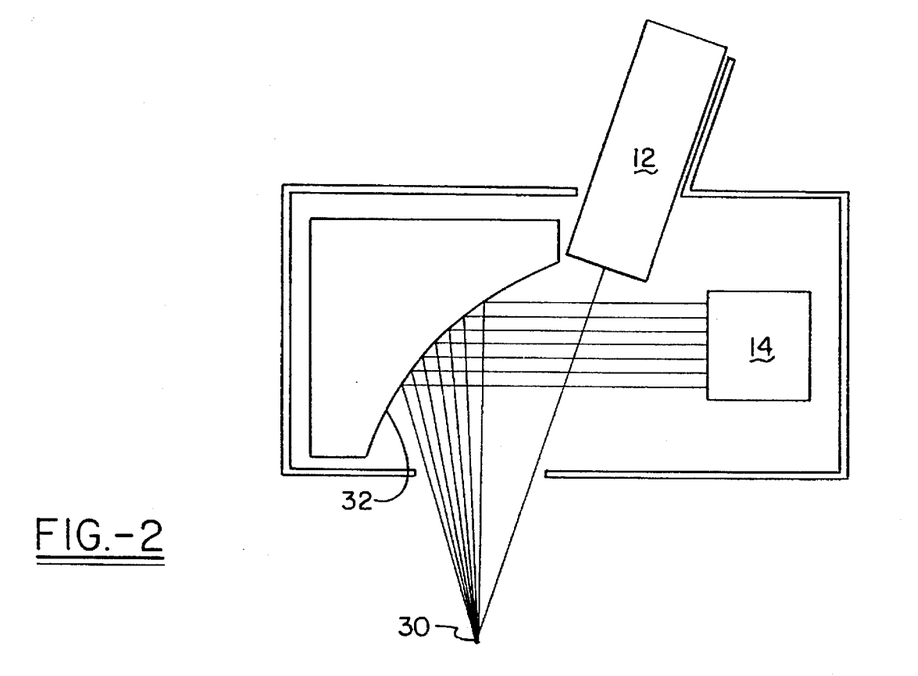
FIG. 2 shows a somewhat schematic diagram of the arrangement of the laser and sound sensors in a preferred embodiment of the invention.

Turning now to FIG. 2, a specific setup arrangement for the laser head 12 and sound head 14 in the apparatus is shown. In the preferred embodiment, it is desirable to focus the light emitted from the laser source to a particular point 30 on the surface being analyzed to yield accurate measurement of the relative position between the laser sensor 12 and point 30. For laser head 12, an emitted light beam is reflected off a surface and detected by a sensor positioned adjacent to the laser source. Changes in the location of a reflected beam on the sensor surface will correspond to changes in surface depth, with resolutions of 2–50 μm. Similarly, the sound head 14 will preferably produce a non-penetrating coherent beam of sound wave pulses, which are focused by an off-axis parabolic mirror 32 to coincide with point 30 on the surface being analyzed, such that both the laser source 12 and sound source 14 will yield information about the same point 30 in simultaneous or discrete data acquisition steps. Alternatively, the focal point of the laser source 12 and sound source 14 may not coincide, requiring further processing to develop data for a particular point on the surface under test.

Figures 3, 4, 5:
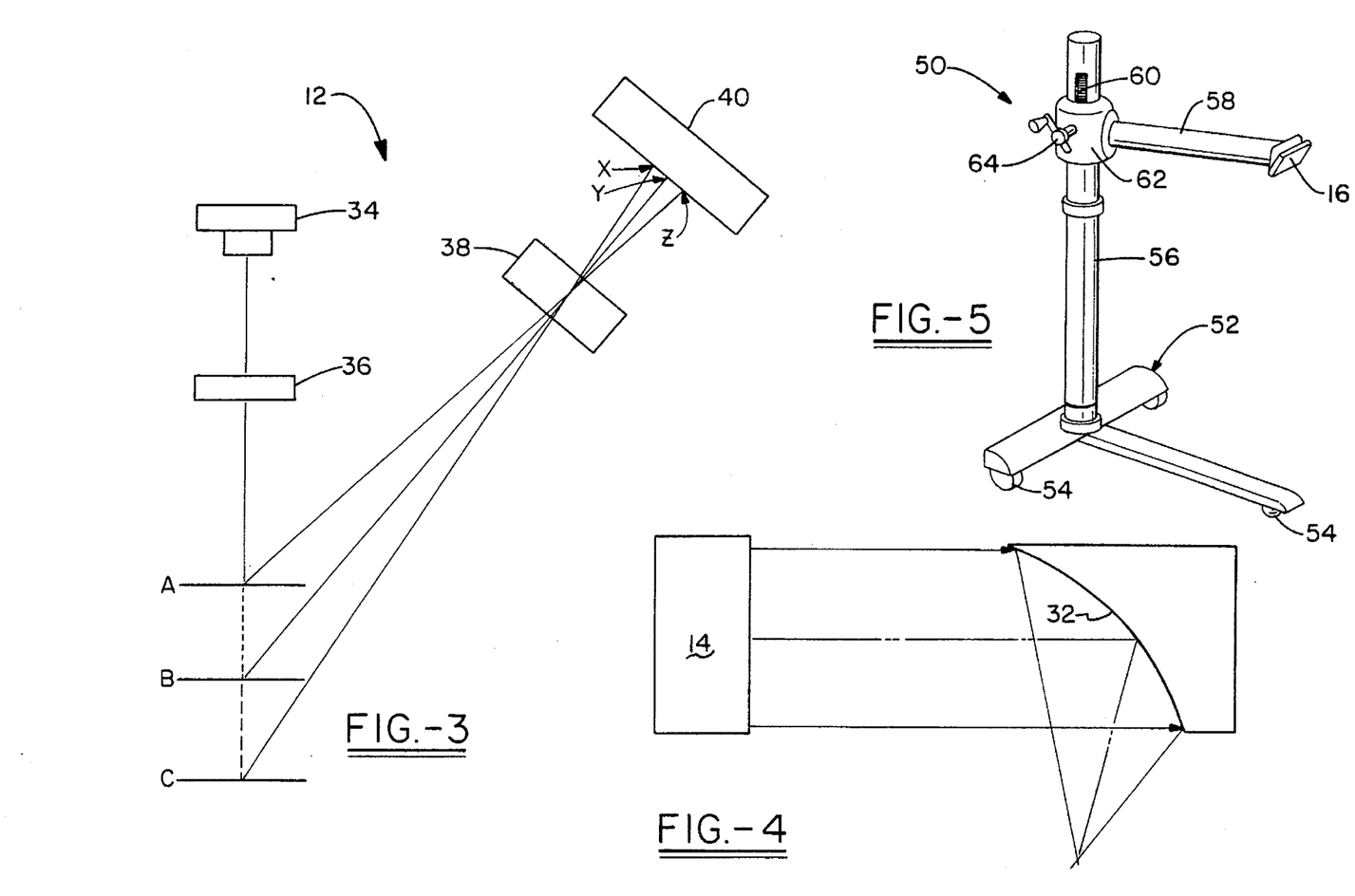
FIG. 3 shows a diagrammatic illustration of the operation of the laser sensor of the apparatus.
FIG. 4 shows a diagrammatic illustration of the operation of the sonic sensor associated with the apparatus.
FIG. 5 shows a portable support stand on which the laser sensor and sonic sensor of the apparatus may be positioned for diagnostic evaluation of a wound using the apparatus.

In FIG. 3, operation of the laser head 12 will be described in simplified terms for the preferred embodiment. The laser sensor operation is based on optical triangulation techniques, allowing the depth of a surface to be quantitatively measured. The basic operating principle of optical triangulation is shown in FIG. 3, wherein light emitted from the laser source 34 associated with laser head 12 is converged to a point on the surface to be detected by means of a converging lens 36. The converged beam of light is then scattered from the surface and refocused by a converging lens 38 associated with a position sensor 40 included in the laser head 12. In the optical triangulation method, the range of measurement will be restricted by the size of the detector, and changes in the location of the reflected beam on the position sensor surface will correspond to changes in surface depth over a scanned surface.

Similarly, as seen in FIG. 4, for the sound head 14, a piezoelectric generator produces a non-penetrating coherent beam of sound wave pulses which are focused by the off-axis parabolic mirror 32 to converge at the surface being analyzed. The point of convergence will correspond closely to the focal point of the mirror 32. Reflected sound wave pulses from the surface will be refocused by mirror 32 and will return to a sound sensor associated with sound head 14 for detection. The time necessary for a sound pulse to return is proportional to the surface-to-sensor distance, and can be used conjunction with laser head 12 to measure surface profiles and/or volumes. Normally, the laser source 12 will be more accurate, and would therefore be preferable in the surface profile and volume measurements accordingly. Additionally, a certain percentage of the sound wave pulses reflected off the surface will correlate to a measure of the surface texture, and the soundhead 14 is therefore used in the apparatus to analyze textural changes over a scanned surface. The operating principle for the sound head 14 for may also be based on a triangulation method, with the distance the sound waves travel being calculated by monitoring the time required for sound waves to return to the sensor head. As sound waves are in actuality pressure waves, the amplitude of the sound wave after reflection on a target surface will also be measured by the sensor head. The difference in amplitude between the incident beam and the reflected beam reveals textural information of the target surface.

In operation of the apparatus 10, a surface to be analyzed will be positioned at a predetermined relative position to the laser head 12 and sound head 14 of apparatus. In accordance with the preferred embodiment, once the surface is positioned relative to the apparatus, the apparatus is then moved relative to the surface in a scanning procedure. Although this is preferred, it is possible to effect movement of the surface relative to the apparatus to accomplish a similar function if desired. As an example, to allow the apparatus 10 to be positioned at a predetermined position relative to a surface to be analyzed, a portable, adjustable stand may be used to house the apparatus 10 as seen in FIG. 5. The portable stand generally indicated at 50 may include a supporting base 52 having a plurality of rollers or wheels 54 thereon to allow positioning of the stand 50 in close relationship to a patient or other surface to be analyzed. On the base 52, an upstanding support member 56 carries an adjustable support arm 58 which extends outwardly to a position which will allow the end of the arm 58 to be positioned relative to a surface to be measured. The arm 58 may be movable on supporting column 56 by any suitable means, such as gear teeth 60 which may cooperate with a meshing gear within the supporting head 62 of arm 58. A rotatable knob 64 may be used to adjust the height of arm 58 to any desired position relative to the surface to be analyzed. The laser head 12 and sound head 14 are positioned and supported on the positioning X-Y table 16, which itself is positioned and supported on the end of arm 58. The X-Y table allows both the sensor heads 12 and 14 to move relative to the surface in a series of indexed scans. Each scan of the apparatus will yield a cross-sectional profile of the surface in voltage units, as well as textural information along the scan line. Scanning and operation is controlled by the sensor head controllers and positioning table controller, and data is recorded and analyzed by means of the interface terminal and computer as previously described. The system will preferably collect data from both the laser head 12 and sound head 14 simultaneously, but also could be utilized to collect data from each sensor head independently on separate scans. The controllers for sensor heads 12 and 14 and positioning table 16 may be provided at a remote location, and coupled to the sensor heads or positioning table accordingly, or may be carried in association with the portable stand 50 to allow the apparatus to be fully portable and functional in a variety of environments. Although the portable, adjustable stand 50 provides one means by which the apparatus can be easily positioned relative to a surface to be analyzed, it should be recognized that a variety of other configurations are possible, and are contemplated within the invention. For example, clinical use of the apparatus may utilize a fixed location for set up of the apparatus, with the ability to bring a patient to the apparatus for diagnostic examination. Included with the apparatus may be patient positioning means to allow a patient or a portion of the patient's body to be positioned in a predetermined location relative to the apparatus. The ability to adjust the position of the sensor heads relative to a particular surface would also be desirable in any type of setup to allow precise positioning of the sensor heads relative to the surface.

Once the apparatus has been located in the predetermined position relative to the surface, scanning of the surface may then be performed. As previously indicated, the apparatus of the invention is advantageously used in the study and quantitative analysis of wounds on skin surfaces, or other surface analysis of the skin to assist in plastic surgery, other surgical reconstructions or the treatment of hypertrophic scarring. For use in analyzing and assessing wound healing or repair, the apparatus allows non-invasive measurement of the surface profile of the wound along with the volume and surface texture to allow an image of the wound to be generated for analysis. Once the apparatus is positioned relative to the wound surface, implementation of scanning is performed by controlling operation of the laser head 12 and sound head 14 to simultaneously or separately collect data from predetermined positions on the wound surface. In the preferred embodiment, the laser and sound wave sensors are mounted on an inverted X-Y positioning table, which is driven by stepper motors and an X-Y controller. By means of the stepper motors, the sensor heads are moved over a predetermined portion of a wound surface in an indexed scan, with the laser sensor 12 and sound sensor 14 simultaneously or independently gathering data at the predetermined points along a scan line. For example, the laser sensor may be operated to emit a laser beam in discrete pulses, with the reflected laser beam being detected by a sensor adjacent to the laser source for each discrete pulse thereon. As the laser source is scanned over the surface, the reflected beam can be detected for a plurality of closely spaced positions along a scan line to yield a surface profile of the entire wound surface along the scanned line. Similarly, the sonic head 14 will produce a coherent beam of sound wave pulses which are directed to the same position on the wound surface and reflected for detection from the same plurality of positions along the scan line. Each scan will give a cross-sectional profile of the wound surface by means of the laser sensor 12 and textural information along this surface profile by means of the sound sensor. A series of indexed scans to cover a predetermined portion of the wound, or the entire wound, may be preformed to allow a three dimensional image of the wound surface to be generated for quantitative analysis. It should be recognized that the amount of data gathered along a scan line, and the number of scan lines used in a series of indexed scans will determine the resolution achievable using the apparatus.

The method for non-invasively analyzing and evaluating wound repair will therefore include the steps of reflecting a laser beam off a portion of the wound surface being analyzed and detecting the reflected beam to determine the position of the portion of the surface relative to the source of the laser beam. Simultaneously or independently, the step of reflecting a coherent beam of sound waves off the same portion of the wound surface and detecting the reflected sound waves will determine at least the texture of the portion of the surface from which the reflected waves are received. These steps are repeated a plurality of times to scan over the surface, and from the acquired data, an image is generated of the scanned surface to quantitatively measure profile and surface textural changes over the scanned surface. In the assessment of wound healing, these steps may be repeated at discrete time intervals, in a time study of the wound, so that images of the wound generated in this manner can be compared to facilitate quantitative analysis and visualization of wound healing during re-epithelialization of the wound surface and during the formation of granulation tissue associated with wound healing.

The method will allow evaluation of wound repair over a predetermined period of time. The time study of the wound will allow quantitative assessment of healing, which may directly correspond to the treatment being utilized for healing of the wound. Assessment of wound repair may therefore be performed on an individual patient basis, or in the study of new treatments or the development of models for evaluation of wound healing. The analysis of wound healing is conducted in vivo, with direct measurement of wound size, mapping of the wound over time, as well as volumetric measurement of the wound and surface textural changes therein being analyzed. Total wound volumes and surface profiles can be accurately determined using a sufficient number of scans of the apparatus, with wound volume being calculated by entering the surface profile data from the series of indexed scans of the apparatus, along with indexing distance and calibration data into an integration software program. Further, the textural analysis of the wound will allow assessment and visualization of wound healing from a soft, subcutaneous wound surface through the re-epithelialization of the wound and the formation of harder granulation tissues during healing. The apparatus provides a methodology for evaluation of wound healing which is non-invasive and allows repeated reproducible measurement of a single wound while not interfering with the healing process. Such a methodology allows quantitative measurement of wound healing in a clinical or other environment while not inducing trauma to the wound which would alter the repair process being studied. The apparatus and method provides high speed data acquisition and real-time analysis if desired, with evaluation of wound repair being measured by changes in wound surface area, wound closure progress as well as measurement of the progression of the epithelial edge of wounds. As in some cases the reparative process of the wound does not directly correlate to assessment of the wound surface area and the advance of the wound edge toward the wound center, the volumetric measurement of the wound will enable assessment of wounds which initiate tissue repair from the wound interior while exhibiting only small changes in surface area. The apparatus and method also provide for rapid evaluation of burn depth to allow assessment of burn treatment for a particular wound. In treatment of burns, a full-thickness burn may require surgical intervention, while partial-thickness burns may be successfully treated by other, less severe methods. Evaluation of burn depth or volumetric measurements would enable the appropriate course of wound treatment to be determined rapidly and accurately. The apparatus and method of the invention may also be used in conjunction with other analysis techniques, such as molecular and cellular repair events which can be monitored by means of transcutaneous gas monitoring or other techniques. The apparatus and method may therefore be utilized to provide early, quantitative evaluation of wounds, as well as a visual record of the entire wound repair process to enable clinicians to design unique treatment therapies and to assess treatment in vivo. The apparatus and methods provide a non-invasive technique for providing quantitative data with increased speed, precision, selectivity and sensitivity, to aid in wound repair assessment or otherwise non-invasively analyzing surface profiles and texture for medical or industrial uses.

Figure 6:
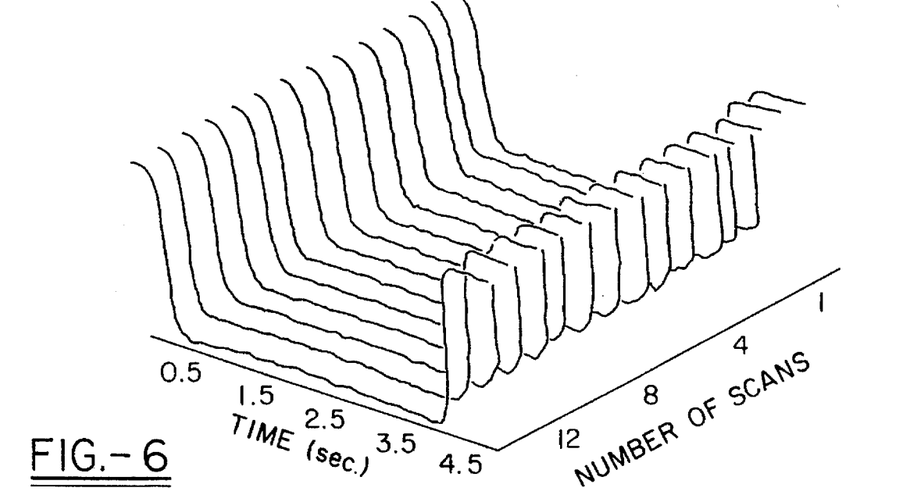
FIG. 6 shows a first example of an image produced by the apparatus for calibration thereof using a known surface configuration.

Turning now to FIG. 6, there is shown an image generated by the apparatus for a surface of known configuration. The apparatus of the invention can be calibrated by performing a scan on a known surface, to accurately reflect volumetric or surface profile information. In FIG. 6, there is shown a reconstructed image of a metal plate having a rectangular groove of known configuration and volume therein. As seen in FIG. 6, a three dimensional image of the rectangular groove in the metal plate is generated using the apparatus, with volumetric measurement of the groove performed. The results from scans conducted over a plurality of different sized rectangular grooves in metal plates, with FIG. 6 showing the image generated for one of such grooves, are given in Table I below:

|  | Volume 1 (ml) | Volume 2 (ml) | Volume 3 (ml) |
|---|---|---|---|
| Actual Volume | 0.1 | 0.2 | 0.3 |
| Measured Volume | $0.08 \pm 2.7 \times 10^{-3}$ | $0.16 \pm 1.5 \times 10^{-3}$ | $0.26 \pm 3.0 \times 10^{-3}$ |
| Ratio (measured to actual) | 0.83 | 0.83 | 0.86 |
| Ratio (relative to volume 1) | 1.0 | 2.0 | 3.1 |

Figure 7:
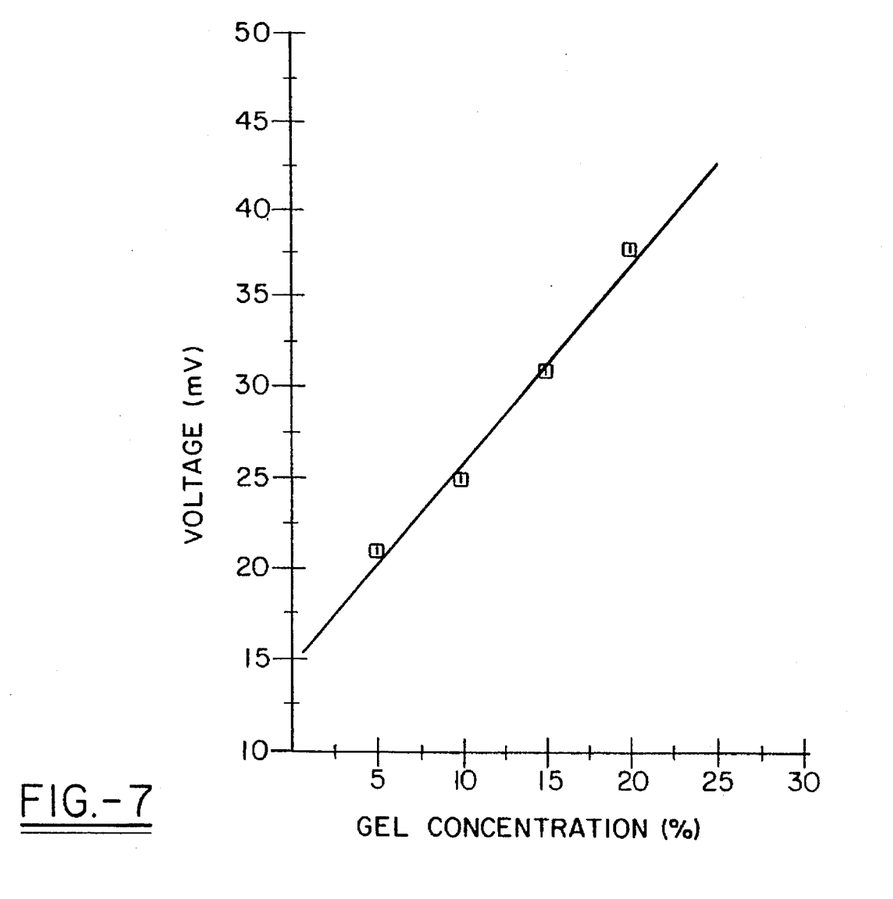
FIG. 7 shows a graph indicating textural analysis for a plurality of surfaces of varying hardness for textural analysis in accordance with the invention.

From the calibration results, it is apparent that both relative and absolute volume measurements are accurate and repeatable in use of the apparatus. Similarly, experimentation regarding textural analysis of a surface using the apparatus was performed, with scans of a plurality of molds filled with different gelatin concentrations giving an indication of textural measurement performance of the apparatus. As seen in FIG. 7, a plurality of scans of the sonic sensor of the apparatus across circular molds filled with different gelatin concentrations were performed, and the corresponding voltage responses of the sonic sensor recorded as represented by the plot of FIG. 7. Variations in amplitude of reflected sound waves in terms of voltage for gels of various concentrations indicate that textural scanning capabilities of the apparatus are both accurate and sensitive to changes in water content in the surface. A linear relationship between the gel concentration and the measured response of the sonic sensor verify the accuracy and repeatability of textural measurements using the apparatus.

Figure 8:
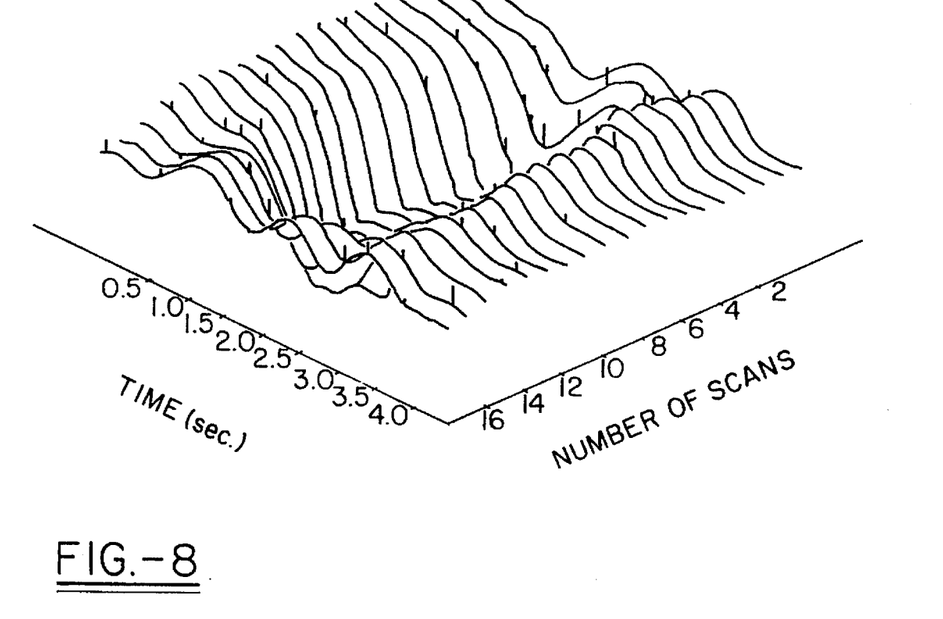
FIGS. 8 and 9 show images produced by the sound source of the apparatus for analyzing textural and profile information.
Figure 9:
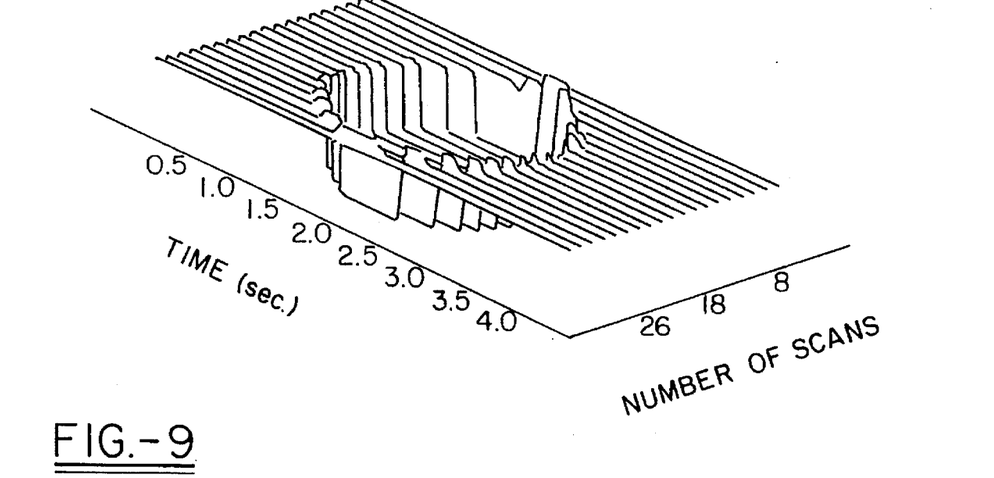

In FIGS. 8 and 9, measurements using the sound source of the apparatus are shown for a known example, being a block of wood having a circular depression formed therein. In the images of the scanned surface using the sound source, both textural and distance measurements are obtained if desired, with FIG. 8 representing textural information about the surface and FIG. 9 representing profile information. In the image of FIG. 8, it is seen that the texture of the surface of the wood block remains relatively uniform until the depression is reached wherein changes in the surface are then observable. The texture of the edges of the formed depression are represented by increased response of the sound signal representing a roughened surface, with the center of the depression being of relatively lower signal strength due to the depression of the surface, but without textural disconformities. These finding are consistent with observation of the sample. Similarly, the profile information which may be gathered using the sound source is shown in FIG. 9, wherein the profile of the circular depression is distinctly revealed in the formed image. The profile information which can be gathered along with textural information using the sound source may supplement the data gathered using the laser source as previously described.

Figure 10:
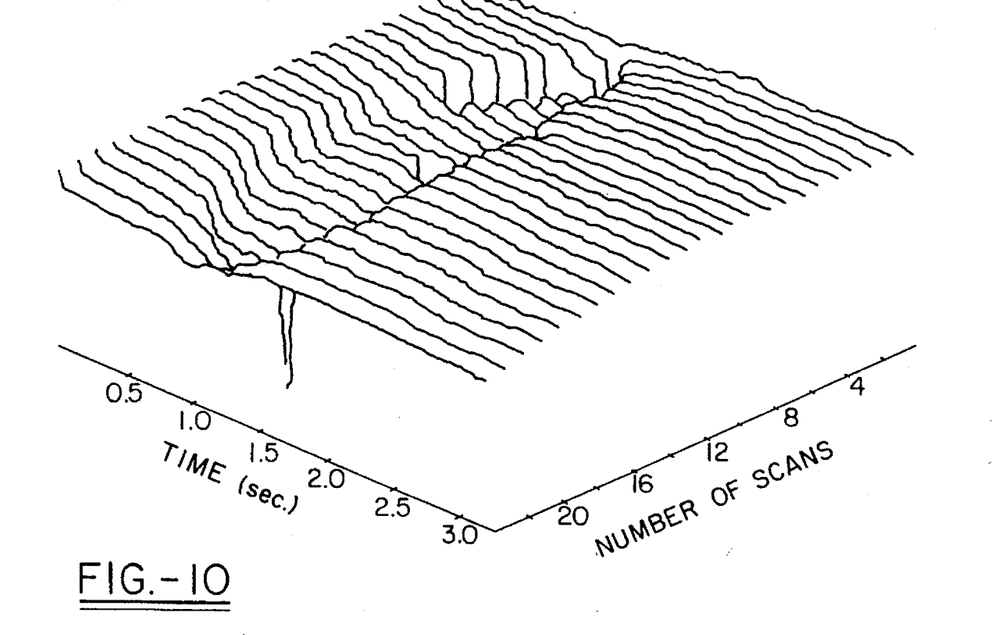
FIGS. 10–12 show images of a wound surface for a dermal wound in an animal.
Figure 11:
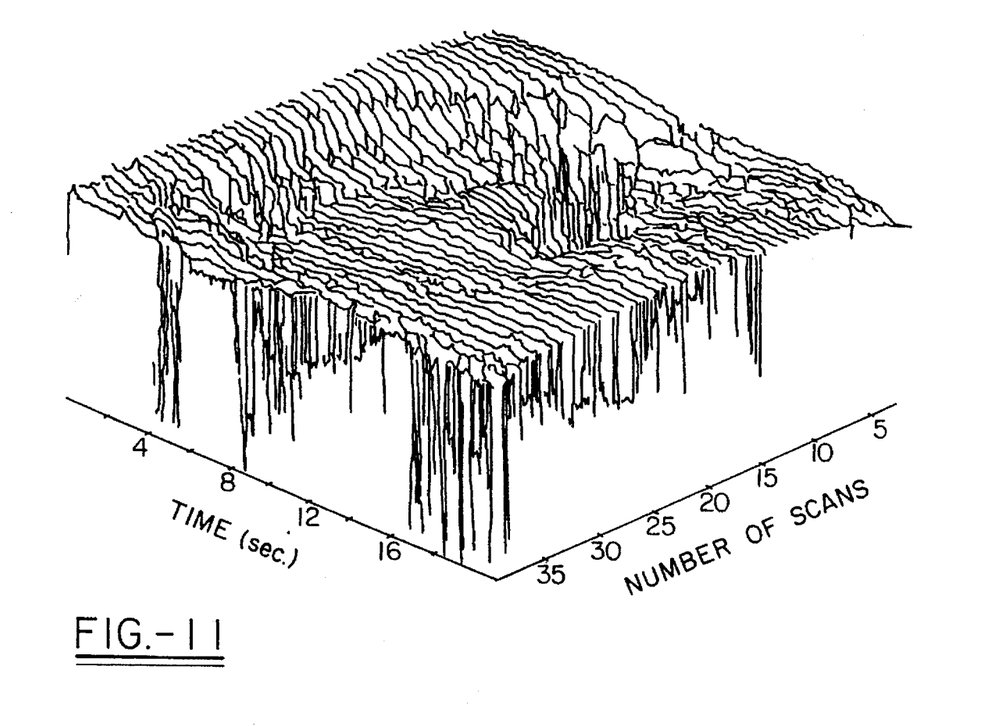
Figure 12:
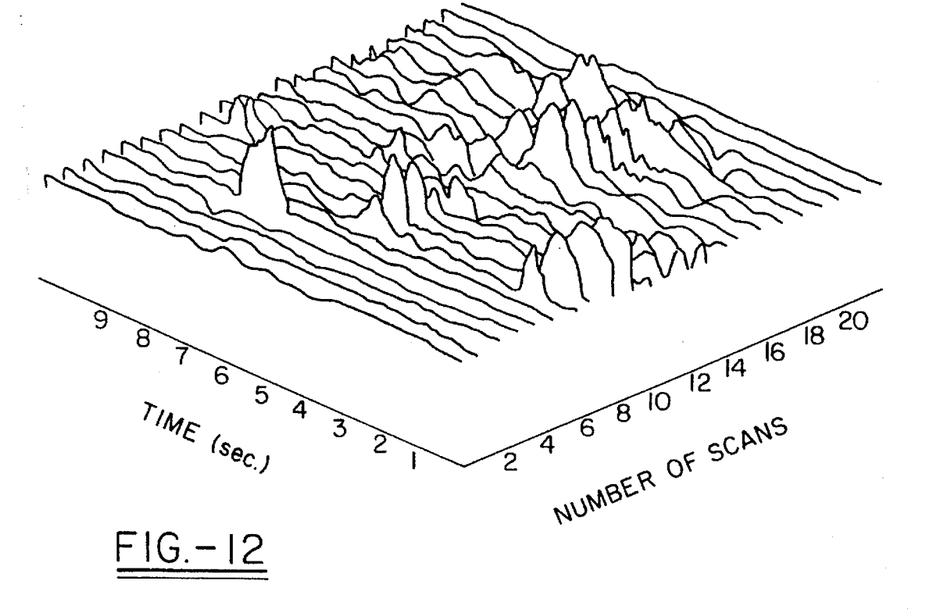

Several examples of use of the apparatus to perform non-invasive analysis of surface profiles and texture for actual wound surfaces are shown in FIGS. 10–12. In FIG. 10, there is shown a three dimensional image generated by a series of laser scans of a full-thickness wound on a rat. Along with surface profile and volumetric measurements generated by the laser scanning, textural data is gathered for analysis. In the wound image shown in FIG. 10, a full-thickness wound was scanned using a large number of scans, and indicating high resolution of the wound image. The scanning procedures may be performed in both the forward and reverse directions on a scanned line, or as an alternative, the system could be designed to collect profile and volumetric data in one scan direction with textural data being acquired in a reverse scan direction, to give a complete wound analysis in a single scan. Another alternative arrangement could collect both profile and textural data simultaneously during scanning in a single direction.

Another example is shown in FIG. 11, showing a high resolution image of a full-thickness circular dermal wound in a rat. The wounds imaged in FIGS. 10 and 11 are two different wounds and each correlated precisely to the actual wound, indicating that the apparatus accurately defines wound profiles thereby enabling volumetric analysis of the wound. Along with the surface profile and volumetric data, textural analysis of the surface is performed to allow quantitative assessment of a wound for a variety of important assessment criteria. As seen in FIG. 12, textural analysis of a full thickness wound on a rat reveals information which can be used to quantitatively assess criteria associated with the wound healing process. In the image of FIG. 12, the normal skin surface is first imaged as appears at the left bottom of the image, indicating slight textural variations, but establishing a base line from which other textural measurements can be assessed. Upon scanning the wound surface at its edge, which appears at trace 4 from the left of the image, it can be seen that a large spike in the data appears, correlating to the re-epithelialization of the wound at its interface with the normal skin surface. The harder tissue formed at this location is reflected in the scan accordingly. Similarly, within the area of the wound itself, the hardening of the wound surface is reflected in the image, indicating the progress of healing and the areas of the wound at which re-epithelialization is occurring at this stage of the healing process. Using the profile and textural images produced in accordance with the invention, a time study of the healing process can be carried out for a particular wound to assess healing of the wound as previously described.

Although the invention has been described in terms of particular preferred embodiments, it should be recognized that various modifications or changes can be made without departing from the spirit and scope of the invention. For example, advances in laser technology may allow higher resolution in the surface profile and volumetric determinations, or the laser source may emit light at a wavelength which may be more compatible for use with human patients. Similarly, the sound head of the apparatus or particular methods of focusing a coherent beam of the sound waves to a predetermined position on a surface may be different than that described in the preferred embodiment. These and other changes are contemplated within the scope of the invention, and the invention is therefore not to be limited by the description herein, but only as defined in the appended claims.

We claim:

1. An apparatus to image a three dimensional surface for analysis of surface profile, volume or surface texture comprising:

a laser source for emitting a predetermined wavelength beam which is reflected off the surface being imaged, a laser detecting means positioned relative to said laser source for receiving the reflected beam to generate a first signal corresponding to the amount of laser energy reflected off said surface, wherein said reflected beam is indicative of changes in the depth of said surface relative to said laser source, a sound source having a frequency less than 1 MHz for generating a coherent beam of sound waves which are reflected off said surface, said sound source not being in physical contact with said surface, a sound detecting means positioned relative to said sound source for receiving reflected sound waves to generate a second signal corresponding to the amount of sound waves reflected off said surface, wherein the reflected sound waves are indicative of at least the texture of said surface, and a process means to receive and independently process said first and second signals and to use said first and second signals to generate an image of said surface.

2. The apparatus of claim 1, wherein, said laser source generates a laser beam at a wavelength which is compatible for use with human or animal skin, so as not to be harmful to said skin, wherein the surface being analyzed is a skin wound surface.

3. The apparatus of claim 1, wherein, said sound source is a sonic sensor emitting a non-penetrating, coherent column of sound waves which are focused to substantially a point by reflecting means such that upon positioning of said point on the surface to be analyzed, reflected sound waves will provide information about said surface at said point.

4. The apparatus of claim 3, wherein, said reflecting means is an off-axis parabolic mirror positioned relative to said sound source for focussing said column of sound waves to substantially said point at a predetermined distance from said mirror.

5. The apparatus of claim 1, wherein, said control means comprises a separate controller for said laser source and detecting means and for said sound source and detecting means.

6. The apparatus of claim 5, wherein, said separate controller for said laser source and detecting means independently controls emission of said laser beam and corresponding detection of said reflected laser energy.

7. The apparatus of claim 5, wherein, said separate controller for said sound source and detecting means independently controls generation of said sound waves and corresponding detection of said reflected sound waves.

8. The apparatus of claim 1, wherein, said sound detecting means receiving said reflected sound waves generates a third signal corresponding the elapsed time between generation of said sound waves and detection of said reflected sound waves which is indicative of changes of the depth of said surface relative to said sound source.

9. The apparatus of claim 1, further comprising, a positioning means on which said laser source and detecting means, and said sound source and detecting means are supported, wherein said positioning means will allow adjustment of each relative to said surface.

10. The apparatus of claim 9, wherein, said positioning means includes a controller which allows adjustment of said laser and sound sources relative to said surface to perform scanning of said surface in a predetermined manner.

11. The apparatus of claim 10, wherein, said controller of said positioning means will operate to perform a series of indexed scans across a predetermined portion of said surface, wherein reflected laser energy and sound waves will be received from a plurality of points on said surface.

12. The apparatus of claim 1, wherein, said laser source and said sound source will focus said laser energy and sound waves to substantially a point on said surface.

13. The apparatus of claim 12, wherein, said point at which said laser energy is focused substantially corresponds to said point at which said sound waves are focused, such that said first and second signals correspond to information from substantially the same point on said surface.

14. A method of non-invasively analyzing surface profiles and surface texture, comprising the steps of:

1) reflecting a laser beam off a portion of the surface being analyzed and detecting the reflected beam to determine the position of said portion of the surface relative to the source of said laser beam, 2) reflecting a coherent beam of sound waves having a frequency less than 1 MHz off said portion of the surface said sound waves and said surface not being in physical contact and detecting the reflected sound waves to determine at least the texture of said portion of the surface, 3) repeating Steps 1 and 2 a plurality of times to produce a predetermined number of scans over a predetermined area of said surface, and 4) generating an image of said scanned surface from said predetermined number of scans to quantitatively measure profile and surface textural changes over said scanned surface, wherein said generating step includes the step of independently processing data acquired from said reflected beam and said reflected sound waves for each of said predetermined number of scans.

15. The method of claim 14, wherein, said laser beam is focused to substantially a point on said surface, and said sound waves are focused to substantially a point on said surface, with step 3 of the method being carried out a plurality of times for different points on said surface.

16. The method of claim 14, wherein, steps 1 and 2 of the method are carried out simultaneously with one another.

17. A method for evaluating wound repair, comprising the steps of:

1) reflecting a laser beam off a portion of a wound surface being analyzed, and detecting the reflected beam to determine the position of said portion of the wound surface relative to the source of said laser beam, 2) reflecting a coherent beam of sound waves having a frequency less than 1 MHz off said portion of the wound surface, said sound waves and said portion of the wound surface not being in physical contact, and detecting the reflected sound waves to determine at least the texture of said portion of the wound surface, 3) repeating Steps 1 and 2 a plurality of times to produce a predetermined number of scans over a predetermined area of said surface of the wound, 4) generating an image of said scanned surface from said predetermined number of scans to quantitatively measure profile and surface textural changes over the wound surface, wherein said generating step includes the step of independently processing data acquired from said reflected beam and said reflected sound waves for each of said predetermined number of scans, and 5) repeating Steps 1–4 at discrete time intervals and comparing the generated images and textural information to quantitatively analyze and visualize wound healing during re-epithialization of the wound surface and the formation of granulation tissue associated with wound healing to evaluate wound repair over a predetermined period of time.

18. The method of claim 17, wherein steps 1 and 2 of the method are carried out simultaneously with one another.

19. The method of claim 17, wherein, said laser beam is focused to substantially a point on said surface, and said sound waves are focused to substantially a point on said surface, with step 3 of the method being carried out a plurality of times fo different points on said surface.

* * * * *